US012285248B2

(12) United States Patent
Harfouche

(10) Patent No.: US 12,285,248 B2
(45) Date of Patent: Apr. 29, 2025

(54) DEVICE FOR MEASURING THE CIRCUMFERENCE OF AN OBJECT, IN PARTICULAR A BODY LIMB

(71) Applicant: Just a New Health, Beauvechain (BE)

(72) Inventor: Joseph Harfouche, Forest (BE)

(73) Assignee: Just a New Health, Beauvechain (BE)

( * ) Notice: Subject to any disclaimer, the term of this patent is extended or adjusted under 35 U.S.C. 154(b) by 939 days.

(21) Appl. No.: 17/428,455

(22) PCT Filed: Feb. 6, 2020

(86) PCT No.: PCT/EP2020/053006
§ 371 (c)(1),
(2) Date: Aug. 4, 2021

(87) PCT Pub. No.: WO2020/161246
PCT Pub. Date: Aug. 13, 2020

(65) Prior Publication Data
US 2022/0104727 A1  Apr. 7, 2022

(30) Foreign Application Priority Data

Feb. 7, 2019 (BE) .................................. 2019/5075

(51) Int. Cl.
*A61B 5/107* (2006.01)
*A61B 5/00* (2006.01)

(52) U.S. Cl.
CPC .......... *A61B 5/1072* (2013.01); *A61B 5/1075* (2013.01); *A61B 5/742* (2013.01)

(58) Field of Classification Search
None
See application file for complete search history.

(56) References Cited

U.S. PATENT DOCUMENTS

2016/0113549 A1* 4/2016 Harfouche ........... A61B 5/1075
600/587
2019/0365284 A1* 12/2019 Harfouche ........... A61B 5/1072

OTHER PUBLICATIONS

Harfouche; The PeriKit: an innovative connected portable device with high level of accuracy and reliability in taking circumferential limb measurements; Veins and Lymphatics 2017; vol. 6:6629 (Year: 2017).*

* cited by examiner

*Primary Examiner* — Jay B Shah
(74) *Attorney, Agent, or Firm* — Renner, Kenner, Greive, Bobak, Taylor & Weber

(57) ABSTRACT

The present invention relates to a device for measuring the circumference of an object, in particular a device for measuring the circumference of a body part.

16 Claims, 5 Drawing Sheets

DEVICE FOR MEASURING THE CIRCUMFERENCE OF AN OBJECT, IN PARTICULAR A BODY LIMB

The present invention relates to a device for measuring the circumference of an object, in particular a device for measuring the circumference of a body part.

Measuring the circumference of body parts such as an arm or a leg is particularly recommended as part of the assessment and follow-up of physiotherapy treatment, for example for the treatment of lymphedemas, i.e. swelling of a part of the body due to the accumulation of lymphatic fluid in the interstitial tissues. Such swelling occurs when the lymphangions that make up the lymphatic vessels are degraded or non-functional (primary lymphedema) or when the lymphatic vessels themselves are damaged or blocked and when lymph nodes have been removed (secondary lymphedema).

More particularly, secondary lymphedemas are a consequence of damage or trauma, for example caused by an accident, surgery, serious infection or radiotherapy or other causes.

This swelling mainly affects the upper and lower limbs such as the arms, feet, legs, thighs and hands, but can also occur in other parts of the body such as the neck, abdomen, back or breasts. It should be noted that secondary lymphedema of the upper limbs is mainly caused by the surgical treatment of the axilla for breast cancer, which consists of the removal of the ganglions in the axilla.

In order to determine to what extent lymphedema (primary or secondary) should be treated, its development should be monitored. For example, when considering secondary lymphedema of the upper limbs, the Clinical Practice Guidelines for the Care and Treatment of Breast Cancer (Clinical Practice Guidelines for the Care and Treatment of Breast Cancer, Canadian Medical Association Journal) recommends measuring the branchial circumference at four points: at the metacarpal-phalangeal joints, at the wrists, and 10 cm downstream and 15 cm upstream of the lateral epicondyles (elbow). A difference of more than 2 cm in circumference between two measurements at one of these four measurement points is considered to justify the treatment of lymphedema. A difference of more than 2 cm in circumference between a body part (e.g. the right arm) with lymphedema and a corresponding body part (e.g. the left arm) without lymphedema also indicates that the swelling should be treated.

It is therefore necessary to have a measuring device or instrument which makes it possible to measure the circumference of body parts periodically and at the same location in order to be able to decide whether or not a treatment for lymphedema is applicable. It is particularly advisable to have a measuring tool which allows precise and reliable measurement since the margin of error must be small and only of the order of a few millimeters, preferably of the order of less than 5 millimeters and more preferably of the order of less than 2 millimeters.

A measurement of the circumference of body parts is also specified in order to observe a decrease in the volume of the skeletal muscles and to monitor the development of this. Such a decrease in muscle volume (or loss of muscle mass) may for example be due to amyotrophy (atrophy and/or disappearance of the striated muscle fiber), sarcopenia (geriatric syndrome) or myopathies (neuro-muscular diseases). These pathologies require monitoring and in particular physiotherapy treatment, during which a precise measurement of the circumference of the body part comprising the muscle in question is essential. Here, too, the development of the circumference of the body part can be monitored by comparing two measurements taken at the same location after a predetermined period of time or by comparing the circumferences of a "healthy" body part and of a corresponding body part with a decrease in muscle volume (loss of muscle mass).

A measurement of the circumference of body parts is also specified in order to observe a decrease in volume when following a diet and during anti-cellulite treatments, in which a thinning of the body part is expected.

A measurement of the circumference of body parts is also specified in order to observe a change in volume during training as part of a strength training program, in which an increase in muscle volume is expected or hoped for.

It is understood that any other condition or pathology causing a variation in the circumference of a body part falls within the scope of the present invention.

Moreover, in Europe, several countries legislate on this subject, such as the Directives of the National Institute for Health and Disability Insurance (NIHDI), which recommend that practitioners (doctors, physiotherapists, etc.) take measurements every 4 cm along the body part which shows swelling or suffers from a decrease in muscle volume. A large number of measurements must therefore be taken and it is therefore necessary to have a measuring tool which, once positioned along a body part, makes it possible to take or carry out measurements at regular intervals on this body part in a reliable, fast, precise and reproducible manner.

Devices for measuring the circumference of an object and more particularly the circumference of a body part are known from WO2014/191513 and WO2018/091462.

Unfortunately, even if the devices according to these prior documents do allow for iterative measurements along body parts, the sliders, which are intended to slide along a slide and which are intended to be connected to measuring elements arranged so as to surround the body part when measuring its circumference, can be the source of slight measurement errors as they can be subject to unwanted displacement at the very moment when an accurate circumference measurement is to be taken. For example, at the very moment when an operator is taking a circumference measurement, which needs to be very precise at the precise location where the measurement is to be taken, an involuntary movement of the patient and/or an involuntary movement of the operator may result in a sliding movement of the slider along the slide, which results in the measurement not being taken at the right place. This is of course problematic since, as indicated above, only a margin of error of the order of a few millimeters can be tolerated for each measurement taken. However, every movement of the slider, even only a few millimeters, can result in a measurement error of several centimeters of the circumference.

The object of the invention is to overcome the disadvantages of the prior art by providing a device for measuring the circumference of body parts which allows fast, simple, precise, reliable and reproducible measurements to be taken regardless of the body part in question, regardless of whether said body part is short or long and whether or not it has curvatures and/or protuberances, at any location along the body part in question. In addition, the invention also aims to provide a measuring device which is reasonably sized, easy-to-handle, light and compact, which constitutes a definite advantage in the medical field where health professionals move from room to room or from one office to another or from one gym to another to see their patients or clients.

In order to at least partially solve the problems of the prior art, according to the invention a device is provided for measuring the circumference of an object, in particular of a body part, comprising:

- a graduated or non-graduated flexible longitudinal element having a first longitudinal direction, arranged so as to be affixed along said object, in particular along said body part, said flexible longitudinal element being connected to a detachable or non-detachable distal strap and/or to a detachable or non-detachable proximal strap, each provided in a plane substantially perpendicular to said longitudinal direction, said flexible longitudinal element comprising different fixed connection areas, and
- a measuring system comprising a connection member which makes it possible to ensure a connection of said measuring system to at least one of the different fixed connection areas of said flexible longitudinal element, said measuring system being in the form of a reel of a graduated or non-graduated flexible measuring element, arranged so as to be affixed and form a loop around said object, in particular around said body part, when said measuring element is in the measuring position, said measuring system comprising:
    - at least one wall and an exit opening arranged so as to allow the exit of at least one unwound part of said measuring element, said at least one unwound part of said measuring element being defined between said exit opening and a distal end of said measuring element, said distal end of said measuring element being provided with a connection element, and
    - a connection means for said connection element of said distal end of said measuring element, said connection member, which makes it possible to ensure a connection of said measuring system in the form of a reel to at least one of the different fixed connection areas of said flexible longitudinal element, being located on a wall of said measuring system between said exit opening and said connection means for said connection element of said distal end of said measuring element.

Preferably, after forming a loop around the body part of which the circumference is to be measured, said connection member is located inside the loop. Optionally, rather than being located inside the loop itself, said connection member may be located in an area adjacent to the exit opening and/or to said connection means for said connection element of said distal end of said measuring element.

Such a device as advocated according to the invention is particularly advantageous and makes it possible to measure the circumference of any body part, at any location on this part, in a fast, precise, reproducible and reliable manner, whether or not said body part has curvatures and/or protuberances, while ensuring that the measurement is actually taken at the intended location once the longitudinal element and the measuring system are properly positioned.

According to the present invention, a simple, precise and fast measurement of the circumference of a body part can be obtained under any circumstances since the flexible longitudinal element comprises fixed connection areas and the measuring system in the form of a reel comprises a connection member which makes it possible to ensure its connection to at least one fixed connection area of the longitudinal element. Within the meaning of the present invention, a "fixed connection area" is an area (a location) on the longitudinal element which is defined by precise, permanent and non-movable positioning. By way of example, such a "fixed connection area" can be a perforation (female member arranged to cooperate with a male member) made in/through the longitudinal element. Within the meaning of the invention, such a "fixed connection area" can also be a catch (male member arranged to cooperate with a female member). Therefore, once the measuring system is connected to the longitudinal element via the connection member, it is connected to a specific location (in an area) of the longitudinal element, from which location (area) it cannot move until a disconnection is effected by an operator, i.e. until the connection member is disconnected from the fixed connection area to which it has been previously connected. This means that, even if the patient and/or the operator makes an involuntary movement during the measurement of the circumference, the measuring system remains in place on the longitudinal element, at the precise location where the measurement must be taken.

In addition, according to the invention, with the connection member being located on a wall of the measuring system between the exit opening and the connection means for said connection element of said distal end of said measuring element, it is particularly easy to affix the measuring element in the form of a loop around the body part of which the circumference is to be measured. In fact, such positioning of the connection member means that it is located inside the loop when it is formed around the object (the body part) of which the circumference is to be measured. The fact that the connection member is located inside the loop means that it does not interfere with either the formation of the loop or its positioning in close contact with the body part of which the circumference is to be measured. This positioning of the connection member as intended according to the invention is such that the measuring element is not in contact with the connection member, which then does not distort the measurement of the circumference as would be the case if the measuring element had to pass over the connection member in order to be able to be connected at the level of the connection means for the connection element of the distal end of the measuring element.

Thus, such positioning of the connection member does not hinder the formation of a loop around the body part, allows the operator to handle the measuring element with ease, and makes it possible to ensure the accuracy of the measurements taken. Once the connection member is connected to a fixed connection area of the longitudinal element, the measuring element is free to be unwound without exerting traction on the longitudinal element and without the risk of the measurement being taken in the wrong location since the connection member ensures that the measuring system (the reel) remains in place, regardless of the manipulations carried out with the measuring element in order to wrap it around the body part. It therefore appears that, unlike a device as shown in FIG. 5 of WO2018/091462, in which the measuring element is connected to a slider, the unwound part of the measuring element is completely free in a device according to the present invention.

In addition, since the longitudinal element is made of a flexible material, it is perfectly suitable, over its full length, to be affixed along body parts directly against the skin, even if these body parts have protrusions and/or hollows. Moreover, since the longitudinal element is made and produced from a flexible material, it can be easily wound up and/or folded, thus minimizing its size and facilitating storage, transportation and handling.

The terms "flexible," or "made of a flexible material," within the meaning of the present invention, mean an element of which the flexibility allows it to follow/envelop, closely and by contact, the surface of the object or of the body part of which the circumference is to be measured, this flexibility also allowing folding, bending or winding.

According to the present invention, precise, simple, reliable and reproducible measurements of the circumference of body parts can therefore be taken under any circumstances, regardless of the body part in question or the location of the body part in question, since the measuring device according to the invention makes it possible to ensure that the circumference measurement will be taken at the precise location envisaged without any displacement of the measuring system and therefore without the measuring element being able to distort the measurement readings taken. As indicated above, such precise, simple, reliable and reproducible measurements of the circumference of body parts are essential in order to eliminate any margin of error which could distort diagnoses and call into question the very principle of measuring the circumference of body parts as a decision-making tool before starting treatment or not.

Preferably, according to the invention, the connection member of the measuring system and/or the different fixed connection areas of the longitudinal element is/are configured such that it or they ensure the provision and holding of said measuring element in a plane perpendicular to the longitudinal direction of the longitudinal element.

Advantageously, according to the invention, said different fixed connection areas are arranged at regular intervals along said longitudinal element.

According to the invention, said connection member of said measuring system is a male or female type member arranged so as to cooperate and provide a connection with at least one of said fixed connection areas of said longitudinal element, which is a corresponding male or female type area.

Advantageously, according to the invention, the connection means for the connection element of the distal end of the measuring element is located at a distance d from said exit opening of the reel, said distance d defined between said exit opening and said connection means being less than or equal to 4 cm, preferably less than or equal to 3 cm, preferably less than or equal to 2 cm, more preferably less than or equal to 1 cm, preferably equal to zero. According to a preferred embodiment, the distance d is equal to zero, which means that the connection means is affixed and therefore in contact with the exit opening of the reel. Such a relative positioning between the connection means and the exit opening of the reel makes it all the more possible to avoid any error and any bias when taking a measurement of a circumference of an object/body part and to measure any circumference no matter how small (for example the circumference of a finger). For example, with the exit opening being delimited by four walls, it is intended according to the invention for the connection means to be placed in direct contact with one of these walls so that the distance d is equal to zero or at least only of the order of a few millimeters.

Preferably, according to the invention, said connection means and/or said connection element are connected by means of a magnet located at said connection means or at said connection element.

Preferably, according to the invention, said longitudinal element comprises sensors which make it possible to determine and define a positioning of said measuring system on the longitudinal element. In particular, these sensors are arranged so that information about the positioning of said measuring system on the longitudinal element can be transmitted to the operator, for example by displaying this positioning on the measuring system and/or by displaying this positioning on an external device (for example a smartphone), with the sensors, the measuring system and/or the external device interacting, for example via an electronic module, such that information relating to this positioning is processed and displayed.

Preferably, according to the invention, the loop formed around said object, in particular around said body part, is provided in a single plane passing through a median longitudinal axis defined along said measuring element. Such positioning of the loop and therefore of the unwound part of the measuring element according to the invention makes it possible to ensure optimum precision of the measurement of the circumference. Indeed, any bias is minimized as soon as the loop is positioned in a single plane.

Advantageously, according to the invention, the measuring system is a spring reel optionally fitted with a locking system and/or a return system for said measuring element. The locking system advantageously makes it possible, after unwinding at least part of the measuring element, to lock the latter in order to facilitate the positioning of the measuring element around the object/body part. Furthermore, following the placement of the measuring element around the object/body part and following the connection of the distal part of the measuring element to the connection means, it is intended that a measuring element return system allows automatic and proper placement of the measuring element around the object/body part of which the circumference is to be measured. Since the unwound part of the measuring element is generally longer than the actual circumference to be measured, for reasons of ease of installation of the measuring device, it must then be ensured that the measuring element perfectly matches the contour of the object/body part, which can be ensured according to the invention by an (automatic) return system for the measuring element, in particular for the unwound part of the measuring element. Of course, any type of suitable reel falls within the scope of the present invention.

Preferably, according to the invention, said measuring system comprises a return system for said measuring element, for example a spring or a motor, which exerts a tension on said measuring element which is associated with a mass of between 5 and 5000 g, preferably between 5 and 3000 g, preferably between 15 and 1500 g, more preferably between 15 and 1000 g, advantageously between 15 and 500 g, and more advantageously between 15 and 150 g.

More preferably, according to the invention, said return system for said measuring element, for example a spring or a motor, is a return system which exerts a tension on said measuring element which is associated with a mass of between 5 and 80 g, preferably between 5 and 60 g, preferably between 70 and 80 g. More preferably still, said return system for said measuring element, for example a spring or a motor, is a return system which exerts a tension on said measuring element which is associated with a mass greater than or equal to 50 g and less than or equal to 5000 g, preferably greater than or equal to 70 g and less than or equal to 5000 g.

The tension to be exerted on the measuring element will be predetermined according to the application targeted by the circumference measurement in order to make it possible to carry out reproducible measurements according to this application (lymphatic edema, traumatic edema, production of compression stockings, etc.).

Advantageously, the measuring device according to the invention comprises a tension sensor, preferably a tension sensor housed in the reel, to detect that the measuring element is tensioned in order to be able to measure the tension.

Preferably, according to the invention, the exit opening of said reel has a section similar to the section of said measuring element. In this way, the exit opening actually guides the measuring element such that it sits correctly around the object/body part of which the circumference is being measured. In particular, the fact that these two sections are similar allows the loop formed around the object/body part to be provided all the better in a single plane passing through a median longitudinal axis defined on the measuring element. Within the meaning of the invention, the smaller the width of the measuring element, the more reliable, precise and reproducible the measurement is; this is achieved in particular by minimizing the gap of the measuring element observed on the front of the forearm, on the leg, on the calf or on any other part of which the shape is not necessarily cylindrical.

Preferably, according to the invention, said distal end of said measuring element provided with a connection element cooperates with said connection means so as to ensure a connection between said connection means and said distal end of said measuring element. Such a connection can be established by means of a male-female system which allows, for example, the connection element present at the distal part of the measuring element to be fitted into the connection means. It is obvious that any other type of system or device capable of ensuring such a connection is an integral part of the present invention, such as fastening using a magnet or fastening using Velcro®.

Preferably, according to the invention, said reel has a window for reading a circumference of an object, in particular a circumference of a body part.

Advantageously, the measuring device according to the invention further comprises:

an electronic measuring module capable of determining a circumference measurement from an unwinding of said measuring element; and display means for displaying a circumference measurement determined by said electronic module.

This embodiment has the advantage of being able to take a measurement quickly: the display means allow the operator to take a direct reading of a circumference measurement. The use of an electronic module capable of determining a circumference measurement also allows better reproducibility of the measurement of the circumference of an object, in particular the circumference of a body part, since the variations due to operator intervention are severely limited by the automation/digitization of the measuring device. Reading the measurement is also easier because the value of the circumference is displayed using the display means.

Preferably, the measuring device according to the invention further comprises communication means for communicating a circumference measurement determined by said electronic module to another electronic device (for example a smartphone). This communication, for example by Bluetooth, of the measuring device with another electronic device via the communication means advantageously makes it possible to avoid the re-transcription of the measurement displayed by the display means by the person carrying out the circumference measurement, for example.

Preferably, the measuring device according to the invention further comprises control means for controlling a transmission (for example by Bluetooth transmission) of a circumference determined by said electronic module by the communication means. The advantage of having control means included in the measuring device is that the operator can determine when he wants the circumference measurement to be communicated, preferably to the display means (for example for a digital display) and preferably to the communication means, so that the measurement is communicated to another electronic device, for example to a smartphone.

Advantageously, the device according to the invention comprises said tension sensor and/or a motor, wherein a tension force can be programmed and a signal (for example an audible signal) alerts the user when this predetermined tension force is reached. This will ensure that the measuring element is sufficiently tight around the object/body part of which the circumference is to be measured or examined. This is particularly advantageous for practitioners such as bandage makers who should be able to apply sufficient tension to achieve a reliable, precise and reproducible measurement or examination, especially for the customized and personalized production of stockings or sleeves.

The present invention also relates to an assembly comprising the measuring device according to the invention and an apparatus capable of communicating with said communication means of said measuring device. The advantage of this assembly is that the circumference measurement is available on an apparatus capable of communicating with said communication means, without having to re-transcribe the measurement and thus avoiding reading and input errors.

Preferably, the assembly according to the invention is characterized in that:

said apparatus comprises a memory comprising data which make it possible to define a position on the longitudinal element, in that said apparatus is capable of communicating with said communication means of said measuring device in order to transmit said data which make it possible to define a position on the longitudinal element, and in that said display means are capable of displaying said data in order to indicate one or more positions on the longitudinal element to a user.

The advantage of this embodiment is that the measuring device, via the display means, makes it possible to indicate to the operator taking the measurement the location at which the measurement should be taken. This allows faster measurement. This also makes it possible to take multiple measurements on the same object or the same body part at intervals which are indicated by the apparatus to the display means of the measuring device and are therefore transmitted to the operator. The operator thus has all the information concerning the measurement he has to take. This allows for a better measurement rate as well as better measurement reliability. The taking of the measurement and the scrolling of the measurement location are controlled via the control means.

Preferably, according to the measuring device in accordance with the invention, the longitudinal element and/or the measuring element can be wound up. For example, the longitudinal element and/or the measuring element can be in the form of a tape measure such as those used in the field of sewing and which are usually made from a flexible plastic material or from paper having a high tensile strength, which allows such tape measures to be wound up either manually or automatically by means of an automatic winding system comprising a return spring, for example. Winding up the longitudinal element and/or the measuring element has the advantage of minimizing the size of the measuring device when not in use, which allows it to be stored in a space-saving form and easily transported. In addition, the fact that the longitudinal element and/or the measuring element can be wound up allows the operator to unwind only the portion that he really needs when taking a measurement, with the unused portion of the longitudinal element and/or the measuring element remaining wound up, being compact and not hindering the movements of the operator.

Advantageously, the measuring device according to the invention comprises a plurality of fixed connection areas. According to the invention, an unlimited number of fixed connection areas can be present on the longitudinal element. When a plurality of fixed connection areas are present on the longitudinal element, the operator or multiple operators can take multiple measurements simultaneously, which saves time, in particular when it is necessary to take periodic measurements at intervals of a few centimeters on a body segment having a relatively large length, for example a leg.

Preferably, according to the measuring device in accordance with the invention, the longitudinal element and/or the measuring element is made of a flexible material such as flexible plastic or paper having sufficient tensile strength.

Preferably, according to the invention, the longitudinal element and/or the measuring element and/or said distal and/or proximal straps are made of a plastic-coated-cloth type material or of a flexible material, for example a silicone or flexible plastic material.

Advantageously, according to the measuring device in accordance with the invention, said distal and/or proximal strap is detachable. For example, said distal and/or proximal strap can comprise a fastening means in the form of a male member of a fastening system to which a female member located on the longitudinal element is fastened. It could also be a Velcro® type of fastening means or any other type of suitable fastening means. Being able to detach the measuring element and/or said distal and/or proximal straps from the longitudinal element makes it possible to minimize the size of the measuring device when not in use, but also to change the measuring element if, for example, this measuring element must have a shorter or greater length or width, which depends on the body part in question.

For example, according to the invention, said proximal strap and/or said distal strap is a reusable Colson® type collar, i.e. it can be closed and then opened. It could also be a Colson® type collar for single use, i.e. it is only intended to be closed. In this case, if the collar is for single use, it will have to be cut in order to detach the measuring device placed around the object of which the circumference has been measured.

Advantageously, according to the measuring device in accordance with the invention, said distal strap and/or said proximal strap is a graduated or non-graduated longitudinal strip having a first and a second end each provided with a closure means and having an open position and a closed position, said open position being a position in which said first and second ends are spaced apart from one other while said closed position is a position in which said first end of said longitudinal strip is folded over said second end.

Advantageously, according to the invention, the distal strap is a strap having both male and female attachment systems placed alternately along said distal strap to facilitate any attachment, regardless of the shape of the object of which the circumference is measured, in particular regardless of the anatomical shape of the body part of which the circumference is measured. For example, this is of interest at the ankle, where a double attachment by crossing can thus be achieved so that the attachment of the distal strap is secure and remains in place to allow precise and reliable measurements to be made regardless of the operator taking the circumference measurement.

Preferably, according to the measuring device in accordance with the invention, said closure means is selected from the group consisting of a male-female system, a magnetic system, a snap closure, a push-button closure or hook-and-loop means, for example of the Velcro® type. Such a closure means is particularly practical since it can be opened and closed quickly with a simple pulling or pressing movement. It is understood that any other type of suitable closure means is also an object of the present invention.

Optionally, according to the invention, said distal and/or proximal strap is mounted on a slider which can slide along the longitudinal element.

According to the invention, the flexible longitudinal element, for example associated with a reel, can be connected to a strap, for example to a proximal strap, by means of a connection element having a base of which the curvature allows it to match the surface of the object of which the circumference is to be measured, for example the surface of a body part. This base can have slots through which the strap (for example the proximal strap) passes in order to be connected thereto. A base can be associated with a plate from which walls between which the reel can be inserted extend, in particular when the flexible longitudinal element is associated with a reel. The plate can comprise a male or female member cooperating with a corresponding male or female member located on the flexible longitudinal element and/or the reel so that the latter can be connected to the plate. Optionally, the plate is rotatable, which makes it possible to orient the flexible longitudinal element and/or the reel, thus facilitating the alignment of the flexible longitudinal element with the object or the body part of which the circumference is to be measured and facilitating the storage of a device according to the invention in a box. Of course, according to the invention, the presence of a reel is not essential and the flexible longitudinal element could be directly connected to the plate or even directly to the base of the connection element if a plate is not present. The presence of a plate is not essential, and the flexible longitudinal element and/or the reel can be directly connected to the connection element.

Further embodiments of the device for measuring the circumference of body segments according to the invention are indicated in the appended claims.

A further object of the invention is a kit for measuring the circumference of an object, in particular of a body part, comprising:

- a graduated or non-graduated flexible longitudinal element having a first longitudinal direction, arranged so as to be affixed along said object, in particular along said body part, said flexible longitudinal element being connected to a detachable or non-detachable distal strap and/or to a detachable or non-detachable proximal strap, each provided in a plane substantially perpendicular to said longitudinal direction, said flexible longitudinal element comprising different fixed connection areas, and
- a measuring system in the form of a reel of a graduated or non-graduated flexible measuring element, arranged so as to be affixed form a loop around said object, in particular around said body part, when said measuring element is in the measuring position, said measuring system comprising:
    - at least one wall and an exit opening arranged so as to allow the exit of at least one unwound part of said measuring element, said at least one unwound part of said measuring element being defined between said exit opening and a distal end of said measuring element, said distal end of said measuring element being provided with a connection element, and a connection means for said connection element of said distal end of said measuring element, a connection member, which makes it possible to ensure a connection of said measuring system to at least one of the different fixed connection areas of said flexible longitudinal element, said connection member being located on a wall of said measuring system between said exit opening and said connection means for said connection element of said distal end of said measuring element.

Such a kit for measuring the circumference of body parts comprises a small number of elements which can be easily and quickly assembled in order to have the device for measuring the circumference of body parts as described above. This kit contains all the essential elements of the present invention.

Other embodiments of the kit for measuring the circumference of body segments according to the invention are indicated in the appended claims.

Other features, details and advantages of the invention will emerge from the description given below, without limitation and with reference to the accompanying drawings.

The present invention also relates to a use of a measuring device according to the invention and to the use of a kit according to the invention for measuring the circumference of an object, in particular for measuring the circumference of a body part.

In the figures, identical or similar elements have the same references.

Figure 1:
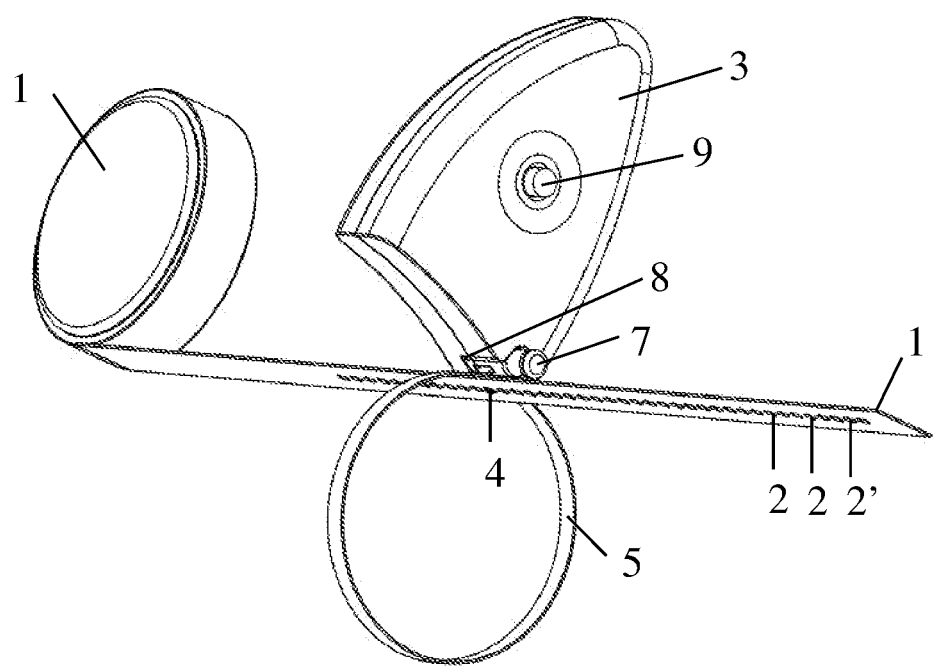
FIG. 1 shows an example of a circumference measuring device according to the invention in its mounted form for measuring the circumference of an object, in particular for measuring the circumference of a body part.

FIG. 1 shows a circumference measuring device according to the invention in its mounted form for measuring the circumference of an object, in particular for measuring the circumference of a body part. This measuring device comprises a reel 10 of a flexible longitudinal element 1 which has a first longitudinal direction and is arranged so as to be affixed along the object, in particular along the body part. This flexible longitudinal element 1 is connected to a distal strap and to a proximal strap (not shown). Furthermore, this flexible longitudinal element 1 comprises different fixed connection areas 2, 2', 2" in the form of perforations located at regular intervals.

In addition, as shown, the measuring device according to the invention comprises a measuring system 3 comprising a connection member 4 in the form of a projection which ensures a connection of the measuring system 3 to at least one of the different fixed connection areas 2, 2', 2" of the flexible longitudinal element 1. This connection member 4, which makes it possible to ensure a connection of the measuring system 3 in the form of a reel to at least one of the different fixed connection areas 2, 2', 2" of the flexible longitudinal element 1, is located on a wall of the measuring system 3 between the exit opening 6 and the connection means 8 for the connection element 7 of the distal end of the measuring element 5.

According to the embodiment shown, the measuring system 3 is in the form of a reel of a flexible measuring element 5 arranged so as to be affixed and form a loop around the object, in particular around the body part, when the measuring element 5 is in the measuring position. As shown, the measuring system 3 has an exit opening 6 arranged so as to allow the exit of at least one unwound part of the measuring element 5, the distal end of the measuring element 5 being provided with a connection element 7 in the form of a cylinder. The measuring system 3 also comprises a connection means 8 for the connection element 7 of the distal end of the measuring element 5, which makes it possible to form and maintain a loop around the object, in particular around the body part of which the circumference is to be measured.

In practice, when taking a measurement of the circumference of a body part, an operator first places the longitudinal element 1 along this body part. To do this, preferably, the longitudinal element 1 is fastened/connected to the body part using a distal strap and/or a proximal strap (not shown), the distal strap and/or the proximal strap preferably being positioned at a fixed anatomical landmark (joint or bone area), which ensures that the distal strap and/or the proximal strap is locked at least in one direction. The operator then connects the measuring system 3 by inserting the connection member 4 in the form of a projection into one of the different fixed connection areas 2, 2', 2" of the longitudinal element 1. The choice of the fixed fastening area 2, 2', 2" is made depending on the location along the body part where the circumference measurement is to be taken. Following insertion/connection of the connection member 4 in the form of a projection into one of the different fixed connection areas 2, 2', 2", the measuring system 3 is fixedly placed on the longitudinal element 1 and the operator can then unwind the measuring element 5 from the measuring system 3 in the form of a reel so as to form a loop around the body part. By inserting and connecting the connection element 7 in the form of a cylinder into the connection means 8, the loop is held around the body part and a measurement of the circumference of said part can be taken.

According to the embodiment shown, the measuring system is provided with a control means 9 for a system for locking and returning the measuring element 5. As indicated above, this makes it possible to ensure easy positioning of the measuring element 5 by locking an unwound part thereof and returning it in such a way that it closely matches, with contact, the body part of which the circumference is to be measured.

Figure 2A:
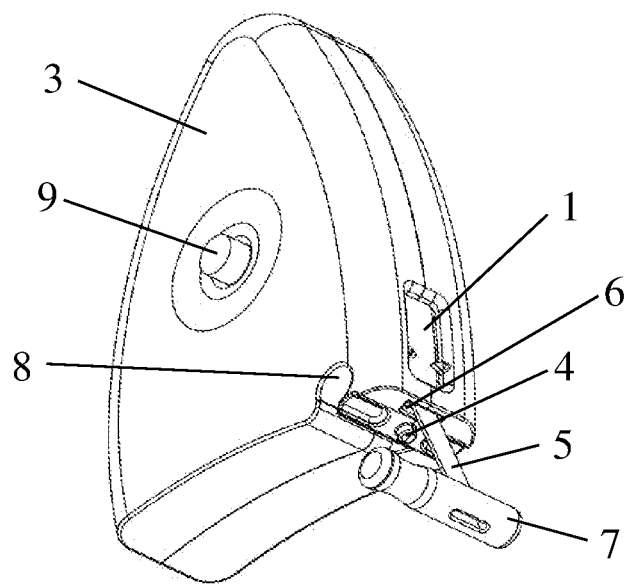
FIGS. 2A, 2B and 2C show an example of a measuring system of a measuring device according to the invention for measuring the circumference of an object, in particular for measuring the circumference of a body part.
Figure 2B:
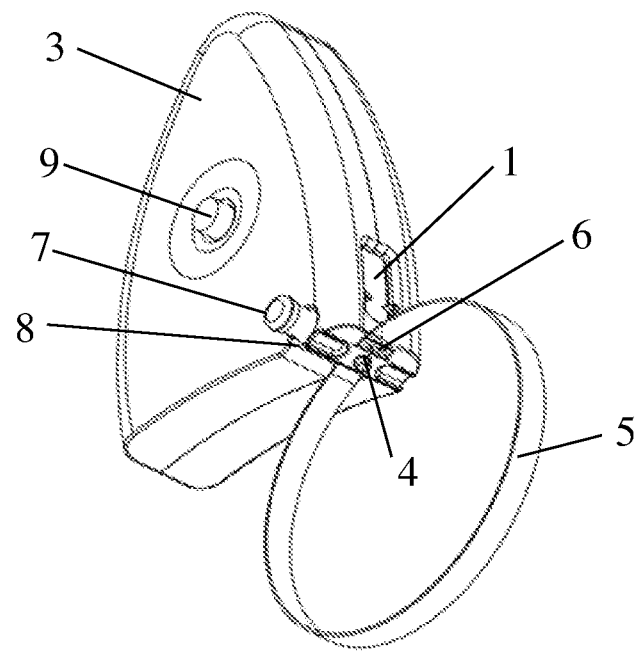
Figure 2C:
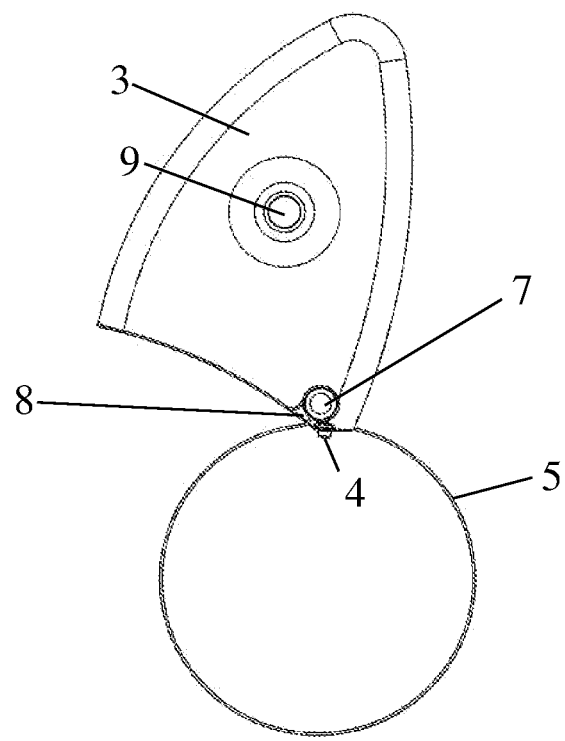

FIGS. 2A, 2B and 2C show the measuring system of a measuring device according to the invention for measuring the circumference of an object, in particular for measuring the circumference of a body part. FIG. 2A shows the unwinding of a part of the measuring element 5 while FIGS. 2B and 2C show the formation of a loop with the measuring element 5, the connection member 4 being located inside the loop. As shown, the measuring system 3 comprises a reading window 11 which makes it possible to read a value of the measured circumference.

Figure 3:
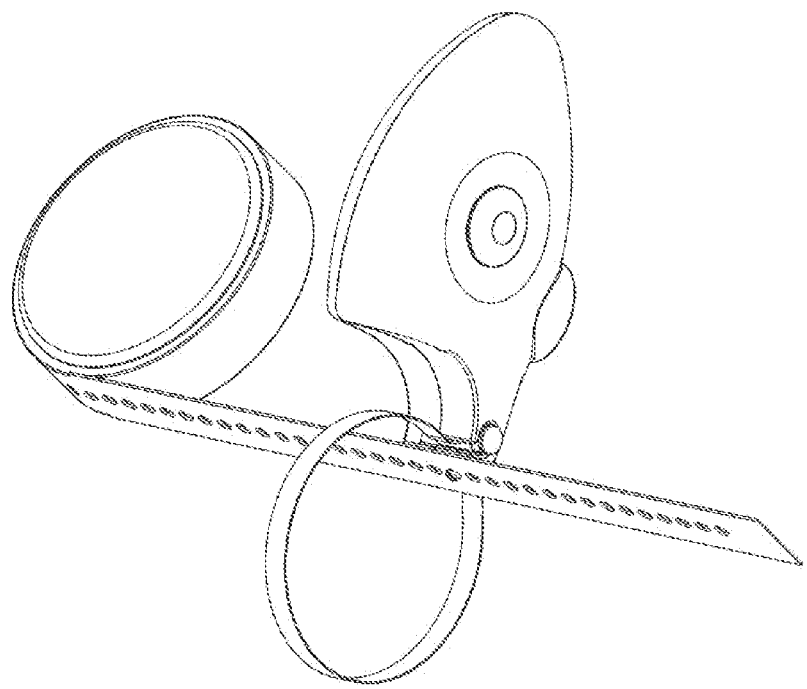
FIG. 3 shows another embodiment of a circumference measuring device according to the invention in its mounted form for measuring the circumference of an object, in particular for measuring the circumference of a body part.

FIG. 3 shows another embodiment of a circumference measuring device according to the invention in its mounted form for measuring the circumference of an object, in particular for measuring the circumference of a body part. This embodiment is identical to that shown in FIG. 1 except for the shape of the measuring system, which has a more pronounced protuberance or projection, at the end of which there is the connection means 8 of the connection element 7, the exit opening 6 arranged so to allow the exit of at least one unwound part of the measuring element 5, and the connection member 4. Such a configuration is preferred for measuring the circumference of thin objects or body parts (for example a finger, however small the circumference), i.e. for measuring the circumference of objects or body parts with a small circumference, without excluding a measurement of larger circumferences. In other words, such a configuration of a measuring system makes the measuring device according to the invention versatile by ensuring precise and reliable measurements regardless of the measured circumference.

Figure 4A:
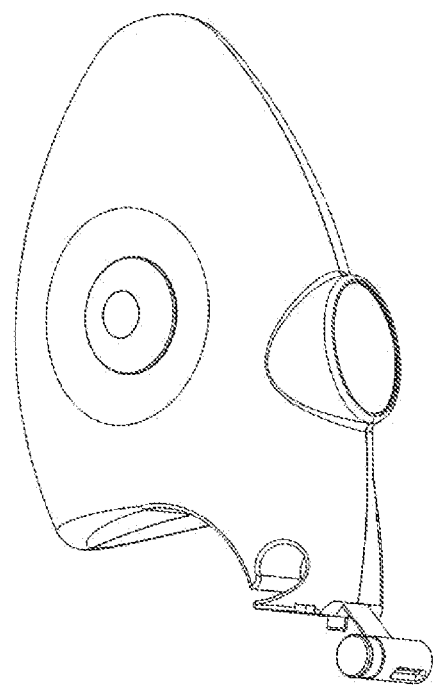
FIGS. 4A, 4B and 4C show another embodiment of a measuring system of a measuring device according to the invention for measuring the circumference of an object, in particular for measuring the circumference of a body part.
Figure 4B:
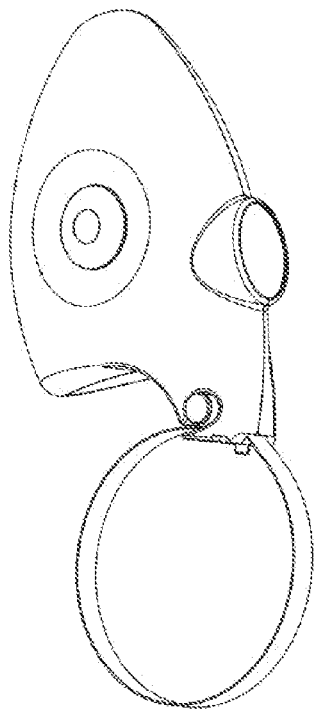
Figure 4C:
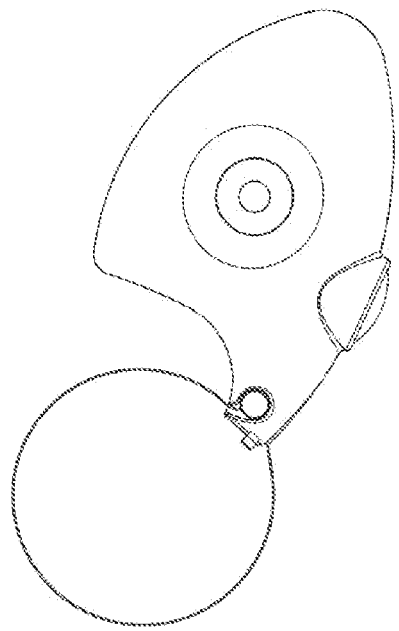

FIGS. 4A, 4B and 4C show another embodiment of a measuring system of a measuring device according to the invention for measuring the circumference of an object, in particular for measuring the circumference of a body part. These embodiments are identical to those shown in FIGS. 2A, 2B and 2C except for the shape of the measuring system, which has a more pronounced protuberance or projection, at the end of which there is the connection means 8 for the connection element 7, the exit opening 6 arranged so to allow the exit of at least one unwound part of the measuring element 5, and the connection member 4. Such a configuration is preferred for measuring the circumference of thin objects or body parts, i.e. for measuring the circumference of objects or body parts with a small circumference, without excluding a measurement of larger circumferences. In other words, such a configuration of a measuring system makes the measuring device according to the invention versatile by ensuring precise and reliable measurements regardless of the measured circumference.

Figure 5:
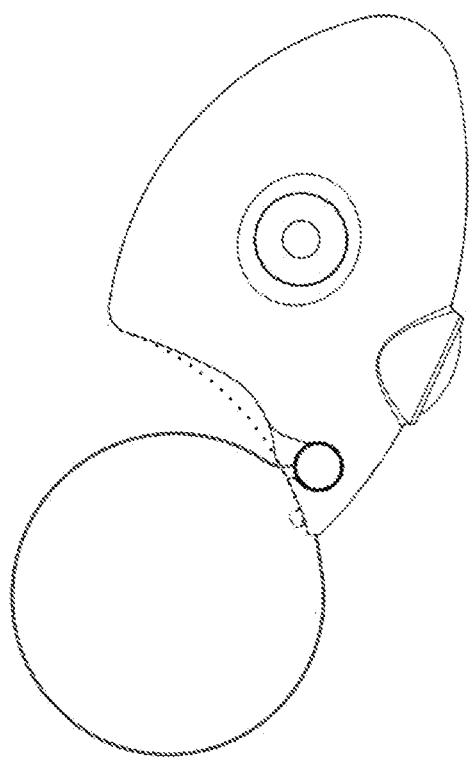
FIG. 5 shows another embodiment of a measuring system of a measuring device according to the invention for measuring the circumference of an object, in particular for measuring the circumference of a body part.

FIG. 5 shows another embodiment of a measuring system of a measuring device according to the invention for measuring the circumference of an object, in particular for measuring the circumference of a body part. Such a configuration is all the more preferred for measuring the circumference of thin objects or body parts, i.e. for measuring the circumference of objects or body parts having a small circumference, without excluding a measurement of larger circumferences. In other words, such a configuration of a measuring system makes the measuring device according to the invention versatile by ensuring precise and reliable measurements regardless of the measured circumference.

Figure 6:
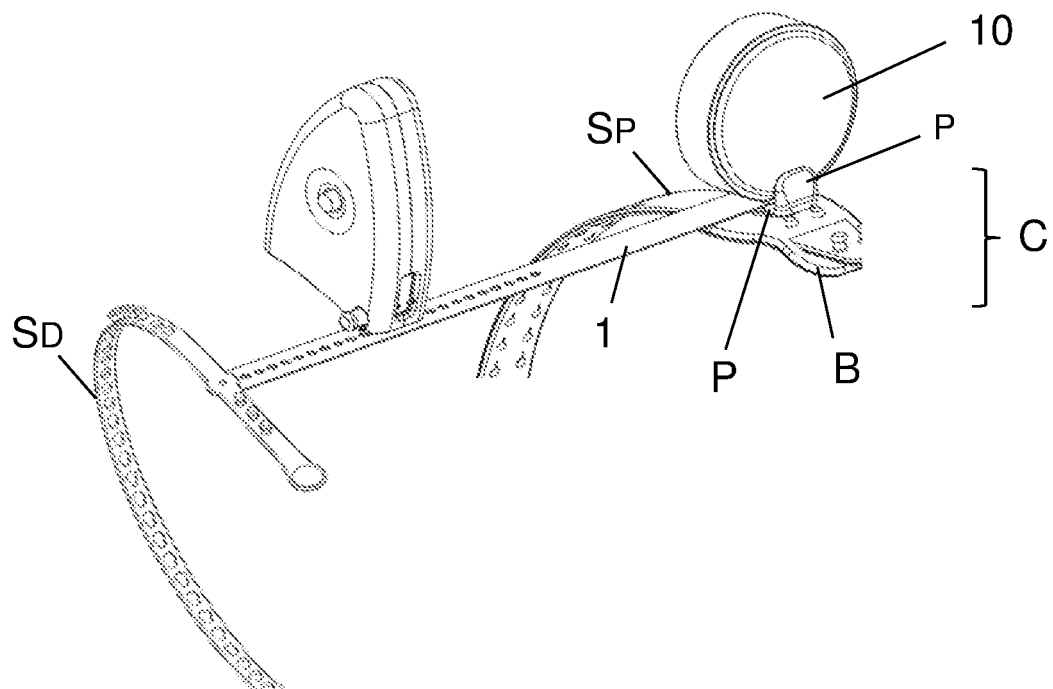
FIG. 6 shows another embodiment of a device for measuring the circumference of an object according to the invention in its mounted form for measuring the circumference of an object, in particular for measuring the circumference of a body part.

FIG. 6 shows an embodiment of a circumference measuring device according to the invention in its mounted form. The same elements as those shown in FIGS. 1 and 3 are repeated but the reel 10 of the flexible longitudinal element 1 is connected to a proximal strap Sp by means of a connection element C. According to the embodiment shown, this connection element C has a base B of which the curvature makes it possible to match the surface of the object of which the circumference is to be measured, for example the surface of a body part. This base B has slots F through which the proximal strap passes in order to be connected thereto. According to the embodiment shown, the base B is associated with a plate PL from which walls p between which the reel 10 can be inserted extend. The plate PL can comprise a male or female member cooperating with a corresponding male or female member located on the reel 10 so that the latter can be connected to the plate P. Optionally, the plate P is rotary. As shown, the circumference measuring device according to the invention also has a distal strap Sd, which comprises male (catches) and female (holes) connection elements.

The present invention has been described in relation to specific embodiments, which have been provided purely for illustration and should not be regarded as limiting. In general, it will be obvious to a person skilled in the art that the present invention is not limited to the examples that have been illustrated and/or described above.

The use of the verbs "comprise," "include," "contain," or any other variant, as well as conjugations thereof, cannot in any way exclude the presence of elements other than those mentioned.

The use of the indefinite article "a" or "an," or of the definite article "the," to introduce an element does not exclude the presence of a plurality of these elements.

The invention claimed is:

1. A device for measuring the circumference of an object, in particular of a body part, comprising:
   a graduated or non-graduated flexible longitudinal element (1) having a first longitudinal direction, arranged so as to be affixed along said object, in particular along said body part, said flexible longitudinal element (1) being connected to a detachable or non-detachable distal strap and to a detachable or non-detachable proximal strap, each provided in a plane substantially perpendicular to said longitudinal direction, said flexible longitudinal element (1) comprising different fixed connection areas (2, 2', 2", ... ), and
   a measuring system (3) comprising a connection member (4) which makes it possible to ensure a connection of said measuring system (3) to at least one of the different fixed connection areas (2, 2', 2", ... ) of said flexible longitudinal element (1), said measuring system (3) being in the form of a reel of a graduated or non-graduated flexible measuring element (5), arranged so as to be affixed and form a loop around said object, in particular around said body part, when said measuring element (5) is in the measuring position, said measuring system (3) comprising:
   at least one wall and an exit opening (6) arranged so as to allow the exit of at least one unwound part of said measuring element (5), said at least one unwound part of said measuring element (5) being defined between said exit opening (6) and a distal end of said measuring element (5), said distal end of said measuring element (5) being provided with a connection element (7), and
   a connection means (8) for said connection element (7) of said distal end of said measuring element (5),
   said connection member (4), which makes it possible to ensure a connection of said measuring system (3) in the form of a reel to at least one of the different fixed connection areas (2, 2', 2", ... ) of said flexible longitudinal element (1), being located on a wall of said measuring system (3) between said exit opening (6) and said connection means (8) for said connection element (7) of said distal end of said measuring element (5).

2. The device according to claim 1, characterized in that said connection member (4) of the measuring system (3) or said different fixed connection areas (2, 2', 2", . . . ) of said longitudinal element (1) is configured in such a way that it ensure the provision and holding of said measuring element (5) in a plane perpendicular to said longitudinal direction of said longitudinal element (1).

3. The device according to claim 1, characterized in that said connection member (4) of said measuring system (3) is a male or female type member arranged so as to cooperate and provide a connection with at least one of said fixed connection areas (2, 2', 2", . . . ) of said longitudinal element (1), which is a corresponding male or female type area.

4. The device according to claim 1, characterized in that said loop formed around said object, in particular around said body part, is provided in a single plane passing through a median longitudinal axis defined along said measuring element (5).

5. The device according to claim 1, characterized in that said measuring system (3) comprises a return system for said measuring element, which exerts a tension on said measuring element (5) which is associated with a mass of between 5 and 5000 g.

6. The device according to claim 5, wherein the mass is between 5 and 3000 g.

7. The device according to claim 5, wherein the mass is between 15 and 1500 g.

8. The device according to claim 5, wherein the mass is between 15 and 1000 g.

9. The device according to claim 5, wherein the mass is between 15 and 500 g.

10. The device according to claim 5, wherein the mass is between 15 and 150 g.

11. The device according to claim 5, characterized in that said return system for said measuring element is a spring or a motor.

12. The device according to claim 1, characterized in that it further comprises:
    an electronic measuring module capable of determining a circumference measurement from an unwinding of said measuring element (5); and
    display means for displaying a circumference measurement determined by said electronic module.

13. The device according to claim 12, characterized in that it further comprises communication means for communicating a circumference measurement determined by said electronic module to another electronic device.

14. A kit for forming a measuring device according to claim 1, comprising:
    a graduated or non-graduated flexible longitudinal element (1) having a first longitudinal direction, arranged so as to be affixed along said object, in particular along said body part, said flexible longitudinal element (1) being connected to a detachable or non-detachable distal strap and to a detachable or non-detachable proximal strap, each provided in a plane substantially perpendicular to said longitudinal direction, said flexible longitudinal element (1) comprising different fixed connection areas (2, 2', 2", . . . ), and
    a measuring system (3) in the form of a reel of a graduated or non-graduated flexible measuring element (5), arranged so as to be affixed and form a loop around said object, in particular around said body part, when said measuring element (5) is in the measuring position, said measuring system (3) comprising:
    at least one wall and an exit opening (6) arranged so as to allow the exit of at least one unwound part of said measuring element (5), said at least one unwound part of said measuring element (5) being defined between said exit opening (6) and a distal end of said measuring element (5), said distal end of said measuring element (5) being provided with a connection element (7), and
    a connection means (8) for said connection element (7) of said distal end of said measuring element (5),
    a connection member (4), which makes it possible to ensure a connection of said measuring system (3) to at least one of the different fixed connection areas (2, 2', 2", . . . ) of said flexible longitudinal element (1), said connection member (4) being located on a wall of said measuring system (3) between said exit opening (6) and said connection means (8) for said connection element (7) of said distal end of said measuring element (5).

15. Use of a kit according to claim 14 for measuring the circumference of an object or for measuring the circumference of a body part.

16. Use of a measuring device according to claim 1 for measuring the circumference of an object or for measuring the circumference of a body part.

\* \* \* \* \*